United States Patent [19]

Janowiak

[11] Patent Number: 4,655,779
[45] Date of Patent: Apr. 7, 1987

[54] AIR SYSTEM PROSTHESIS FOR AMPUTEES

[76] Inventor: Christopher S. Janowiak, 320 N. Washington, Ypsilanti, Mich. 48197

[21] Appl. No.: 793,217

[22] Filed: Oct. 31, 1985

[51] Int. Cl.⁴ .............................................. A61F 2/80
[52] U.S. Cl. ..................................................... 623/37
[58] Field of Search ...................... 623/33, 34, 35, 36, 623/37; 128/DIG. 20

[56] References Cited

U.S. PATENT DOCUMENTS

| | | | |
|---|---|---|---|
| 3,393,407 | 7/1968 | Kandel | 623/37 |
| 3,671,980 | 6/1972 | Baird | 623/37 |
| 3,889,301 | 6/1975 | Bonner | 623/37 |
| 4,232,459 | 11/1980 | Vaccari | 36/3 R |

Primary Examiner—Richard J. Apley
Assistant Examiner—James Prizant
Attorney, Agent, or Firm—Cullen, Sloman, Cantor, Grauer, Scott & Rutherford

[57] ABSTRACT

An air system prosthesis for amputees includes a hollow body with stiff peripheral walls and an open end and a cup shaped partition defining with the walls a first socket. A hollow stump support second socket with stiff peripheral walls is snugly nested within the first socket upon the partition. The second socket includes spaced apart inner and outer walls with cup shaped closed ends interconnected and hermetically sealed at their other ends defining a continuous air chamber between the inner and outer walls adapted to snugly and frictionally receive a human stump. A manually operated air pump and pressure relief valve is mounted upon the outer wall having a normally closed air passage adapted for applying pressurized air to the chamber and for selectively exhausting air therefrom. A modified prosthesis includes a partition wall having a cup shaped closd end spaced from the inner wall and connected and hermetically sealed at its other end to the inner wall defining a liquid chamber adpated to retain a quantity of liquid material for cushioning the stump within the second socket.

5 Claims, 11 Drawing Figures

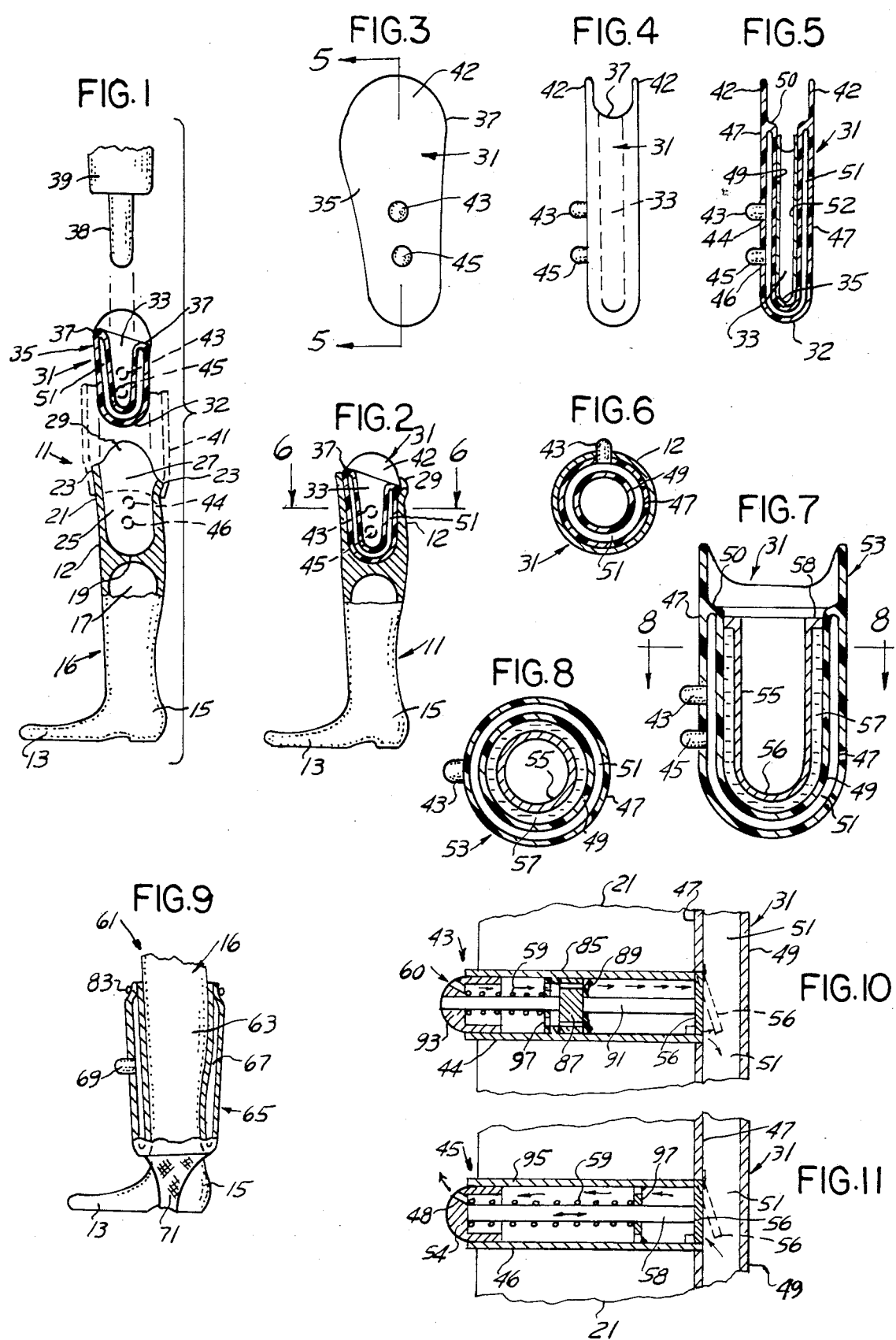

AIR SYSTEM PROSTHESIS FOR AMPUTEES

FIELD OF THE INVENTION

The present invention is directed to a prosthesis for amputees and more particularly an artificial arm or leg assembly which includes a removable stump supporting socket cooperatively and frictionally receiving a human stump.

BACKGROUND OF THE INVENTION

Heretofore conventionally there have been employed prosthesis for the stump of an amputee and wherein there has been employed a prosthesis body of a predetermined cross sectional shape including stiff peripheral walls, has a partition defining with the walls an elongated first socket and wherein there is usually a depending flexible foot or arm. Removably positioned within the first socket is a hollow elongated stump support second socket of a stiff material having a cup shaped bottom and continuous peripheral side walls adapted to supportably and frictionally receive a human stump. One of the disadvantages of conventional prostheses is that often there is not a proper and sufficient fit of the stump within the second socket. Also there is a loose instead of a preferable snug tight fit between the stump and the second socket. Another disadvantage of conventional prostheses is that after long use pain developes, sometimes of a severe nature.

Often there is an improper fit between the stump and the stump receiving socket such as to render walking difficult. Often in cold temperatures, the cold from the exterior is transmitted through the sockets to the stump.

SUMMARY OF THE INVENTION

Important feature of the present invention is to provide an air system prosthesis and wherein there is an improvement by providing a double walled stump support socket hermetically sealed at its open end and defining an air chamber between the inner and outer walls into which pressurized air is applied.

As another feature, applied to the outer wall of the stump support socket is a manually operated or finger operated air pump having a normally closed air inlet passage therein whereby controlled amounts of pressurized air may be directed into the air chamber and applied uniformly to the interior of the chamber, to the prosthesis walls and to and along the length of the stump frictionally retaining the stump.

A further feature includes a pressure relief valve upon the outer wall of the stump support socket for selectively exhausting air from the air chamber.

As another feature the manually operated pressure relief valve may be a part of and associated with the finger operated pump and wherein said pump and relief valve project outwardly of the outer wall of the stump support socket and through a corresponding opening in the wall of the prosthesis body for selective manual access to the pump and relief valve.

A further feature is to provide for the stump support socket a doubled wall envelope closed at one end and with the inner and outer walls of the envelope at their outer ends interconnected and hermetically sealed to define a pressurizable air chamber and to provide a variable distribution of pressurized air within the chamber around the stump for a proper and comfortable fit of the stump at all times, for adjusting the fit throughout the day, to function as an insulator during cold weather and for frictionally anchoring the second socket within the first socket and providing a yieldable cushion support for the stump and for alleviating 10 to 60% of pain frequently encountered after long use of the prosthesis, particularly when used as a leg prosthesis.

Another feature includes upon the inner wall of the stump receiving socket a partition wall having a cup shaped closed end and at its outer end connected to and hermetically sealed with respect to the inner wall of the stump support socket. This provides an enclosed fluid chamber adapted to receive a quantity of liquid material for improving the fit between the stump and the stump support socket and for cushioning the stump therein.

Another feature includes upon the calf portion of the prosthesis body adjacent a foot portion, an elongated imperforate double walled sealed envelope stocking having an ankle strap at one end and a resilient band at its other end engagable with the calf portion of the prosthesis. A normally closed air valve is applied to the stocking envelope adapted to receive pressurized air for inflating said envelope along its length for better defining the calf portion of the prosthesis.

These and other features and objects will be seen from the following claims in conjunction with the appended drawings.

THE DRAWINGS

FIG. 1 is a fragmentary partly sectioned exploded view of present air system prosthesis.

FIG. 2 is a partly sectioned side elevational view of the prosthesis of FIG. 1 with the stump receiving socket assembled within the prosthesis body.

FIG. 3 is a side elevational view of the stump support socket on an increased scale.

FIG. 4 is an end elevational view thereof.

FIG. 5 is a longitudinal section of the stump support socket taken in the direction of arrows 5—5 of FIG. 3.

FIG. 6 is a plan section taken in direction of arrows 6—6 of FIG. 2.

FIG. 7 is a vertical section of a modified stump support socket including a pressurized air chamber and a liquid chamber.

FIG. 8 is a section taken in the direction of arrows 8—8 of FIG. 7.

FIG. 9 is a fragmentary partly sectioned elevational view of a modification which includes an inflatable stocking envelope for the calf portion of the prosthesis.

FIG. 10 is a vertical section of the finger operated pump shown in FIG. 5, on an increased scale.

FIG. 11 is a similar view of a finger operated pressure relief valve shown in FIG. 5.

It will be understood that the above drawing illustrates merely a preferred embodiment of the invention, and that other embodiments are contemplated within the scope of the claims hereafter set forth.

DETAILED DESCRIPTION OF AN EMBODIMENT OF THE INVENTION

Referring to the drawing, the present air system prosthesis for amputees is generally indicated in the exploded view, FIG. 1, which includes prosthesis 11 including a partly resilient foot portion 13, a resilient insert heel portion 15 of increased resiliency and a chamber 17. An arm prosthesis is equivalent.

Prosthesis body 16 constructed of a hardened rubber includes the peripheral exterior walls 21 similar to the shape of a human leg or arm and terminating in the peripheral outwardly curved top portions 23 providing an outwardly flared open end or throated portion 27. Cup shaped concave partition 19 within body 16 defines with walls 21 a first socket 25. Said socket includes a pair of spaced outwardly diverging lateral wings 29.

A stump support second socket 31 constructed of a hardened rubber has a cup shaped convex bottom wall 32 adapted for supported registry with concave partition 19 when assembled within the first socket 25, FIG. 2. Stump support socket 31, sometimes referred to as a second socket, includes a stump receiving chamber 33 defined by exterior peripheral walls 35 of a stiff material such as rubber, for illustration.

The peripheral side walls 35 terminate at their outer ends in the outwardly curved top portions 37 defining a throated opening adapted to cooperatively and frictionally receive stump 38 for the human leg 39 fragmentarily shown in the exploded view, FIG. 1, or for an arm.

In use with the stump 38 snugly nested within the stump support socket 31 and with the stump support socket frictionally nested within socket 25 of the prosthesis body, there is shown in FIG. 1, in dash lines a conventional connector rubber sleeve 41 which overlies the assembled parts and wherein an upper portion of the sleeve resiliently engages and surrounds a portion of the human leg 39 adjacent the stump. The opposite end portion of the resilient connector sleeve 41 extends around and resiliently engages an upper portion of the prosthesis walls 21. Such sleeve could be applied to an arm and arm prosthesis.

As shown in FIGS. 3, 4 and 5, the outwardly curved ends 37 of the stump support socket 31 terminate in a pair of opposed outwardly inclined wings 42. When the second socket 31 is assembled within the first socket 25, the corresponding outwardly curved portions 37 of the second socket cooperatively bear against the outturned portions 23 of the first socket.

The corresponding wings 42 of the second socket cooperatively bear against the adjacent wings 29 at the upper end of body 16, FIG. 2. Second socket 31 is of a double wall envelope construction.

A manually operable finger pump 43, shown in detail in FIG. 10, is mounted upon the outer wall 47 of stump support socket 31 and is adapted to project through a corresponding clearance aperture 44, schematically shown in FIG. 1. Actually said aperture is on the opposite or medial side of the prosthesis, not shown in FIG. 1.

The present and improved stump support socket 31 includes spaced apart inner and outer walls 47 and 49 which are interconnected and hermetically sealed at their one ends as at 50, FIG. 5, to define a continuous air chamber 51 between the inner and outer walls and between the bottoms thereof. Socket 31 is adapted to snugly and frictionally receive stump 38.

The finger operated pump 43 is connected to outer wall 47 and includes a normally closed air inlet 60, FIG. 10, which communicates with air chamber 51. Said pump on intermittent activation is adapted for applying pressurized air to chamber 51. Air pressure is applied to and around air chamber 51 throughout its height for registry with the prosthesis walls 21 and to and along the length of stump 38.

A finger operated pressure relief valve 45, FIG. 11, which could be assembled as a part of pump 43 is mounted upon outer wall 47 of socket 31 and includes a normally closed one way air outlet 48 which communicates with air chamber 51 for selectively exhausting air therefrom.

The pump 43 and pressure relief valve 45, as shown in the illustrative embodiment are spaced apart, project outwardly from outer wall 47 into and through a corresponding opening or openings 44 and 46 within wall 21 of prosthesis body 16 for selective manual access thereto.

In the illustrative embodiment and for clarity, there is shown spaced apart pump 43 and relief valve 45. It is contemplated as an equivalent construction that relief valve 45, shown in detail in FIG. 11 on an increased scale, may form a part of pump 43, as in a tire valve.

The primary function of pump 43 is to provide by manual or finger inward movements the pumping of pressurized air through a corresponding normally closed air inlet 60 and through outer wall 47 for feeding pressurized air into chamber 51.

The corresponding pressure relief valve 45 on outer wall 47 is shown on an increased scale in FIG. 11, includes a normally closed air exhaust passage 48 in conjunction with a push buttom 54 and valve element or flap 56 such that inward projection thereof through rod 58 connected to said flap opens the air exhaust passage 48 sufficiently to permit controlled exhausting of air from air chamber 51. Compression spring 59 returns push botton 54 to a closed position closing flap valve 56.

The continuous walls 21 forming a portion part of body 16 of the prosthesis 11 are of different but predetermined cross sectional shapes throughout their height. Peripheral walls 35 of the stump socket 31 are of similar and corresponding cross sectional shape throughout its height so as to cooperatively and snugly be received within socket 25 of the prosthesis body.

The cross sectional shapes of the walls 21 and 35 are sufficiently irregular so that there is only one way for assembly of socket 31 into socket 25. This provides a snug assembly and frictional engagement of the sockets.

In the illustrative embodiment the respective walls 21 and 35 of the first and second sockets are relatively stiff and may be constructed of a suitable rubber, of any desired color such as brown, and wherein there is a snug assembled relationship between the stump receiving socket 31 and socket 25.

As viewed in FIG. 5, the inner and outer walls 49 and 47 of the stump receiving socket are sufficiently spaced apart, but hermetically sealed together at their one ends to define continuous air chamber 51 between the inner and outer walls and between the bottom portions thereof, adapted to snugly and frictionally receive human stump 38 of a leg or arm.

The selective activation of pump 43 and pressure release valve 45 provides a uniform distribution of variable pressurized air within chamber 51 around stump 38 for a proper and comfortable fit of the stump at all times, for adjusting the fit throughout the day during use, to function as an insulator during cold weather, for frictionally anchoring the second socket 31 within the first socket 25, for providing a yieldable cushion support for the stump 38 such as alleviates 10 to 60% of pain frequently encountered after long use of the prosthesis. A similar pump and valve construction is shown in U.S. Pat. No. 4,232,459. Its construction and operation, to the extent necessary to understand the operation of pump 43 and valve 45 is incorporated herein by reference as one way of pumping air into chamber 51 and releasing air therefrom.

The present prosthesis including socket 25 and stump socket 31 are preferably constructed of a hardened material such as rubber of a limited resiliency and come in four different sizes: small, medium, large and extra large. Applied to the interior of inner wall 49 of the stump socket 31 is a lining 52 of thin polyester or a wool fabric considered equivalent in this disclosure, and adapted to cooperatively receive stump 38.

In the illustrative and preferred embodiment of the present invention, the pump 43 and pressure relief valve 45 are located upon the medial or inner side of the prosthesis, though shown upon the opposite side in FIG. 1 for clarity, extend through corresponding apertures 44 and 46 in prosthesis body 16 and extend outwardly of its outer wall 21.

A modified stump support socket 53 is shown in FIG. 7, on an increased scale, and provides upon the interior of said socket a liquid chamber 57. There is provided upon the stump receiving socket 31 and inwardly of its inner wall 49 a partition wall 55 having a cup shaped bottom 56 spaced within the bottom of stump socket 31 spaced apart from the inner wall 49. Said partition wall at its upper end is connected to wall 49 and hermetically sealed as at 58, FIG. 7. This defines a peripheral liquid chamber 57 interposed between inner wall 49 and stump 38 when assembled thereinto.

In the illustrative embodiment the chamber 57 is adapted to contain water or liquid or fluidized material to thereby provide uniform pressure distribution between inner wall 49 of the stump support socket 31 and partition 55 for cushioning of stump 38 along the sides and upon the bottom thereof to provide an increased resiliency and cushion support for said stump and for alleviating much of the pain often encountered with continued use of the prosthesis. This provides for an improved distribution of controlled pressure upon and around said stump and for cushioning the stump within socket 31.

A prosthesis modification is shown at 61 in FIG. 9, adapted to enclose the hard calf portion 63 of prosthesis body 16 which terminates in foot 13. There is provided an elongated inflatable impervious double wall envelope 65 which is sealed together at its opposite ends to define a sealed annular air chamber 67. A suitable valve 69, similar to valve 45 of FIGS. 5 and 11, is mounted upon outer wall of inflatable envelope stocking 65. Said valve is adapted to receive pressurized air for delivery throughout air chamber 67 and to provide a more human appearing calf portion for the prosthesis other than the relatively stiff appearing and hardened conventional calf 63 of the prosthesis.

U shaped heel strap 71 depends from the lower end of the inflatable envelope stocking 65 and extends around the heel portion of the prosthesis foot 13. An elastic band 83 extends around or is retained within upper end portions of envelope stocking 65 and resiliently engages an upper portion of the prosthesis calf 63.

The advantage of the present inflatable calf enclosing stocking envelope 65 is to cover the otherwise artificial looking stiff and hard calf member 63 of the prosthesis and to provide a more human appearing calf inflated sufficiently to provide a human appearance.

Pump 43, FIGS. 5 and 7, is shown on an increased scale in FIG. 10 and includes a cylinder 85 connected at its inner end to the outer wall 47 of socket 31 and projects through a corresponding aperture 44 in the prosthesis wall 21. Piston 87 is reciprocally mounted within said cylinder, and is connected to piston rod 91 and includes a flexible wiper 89 upon the interior of said cylinder. The outer end of said piston rod projects into and is secured to pump button 93 having an apertured air inlet 60. The inner end of piston rod 91 is connected to pivotal flap valve 56 which is normally closed.

Coiled spring 59 surrounds a portion of rod 91 and is interposed between button 93 and stop washer 97. Intermittent limited inward movements of button 93 and connected piston 87 pump air through passage 60 past piston 87 and flexible wiper 89 and into chamber 51. Spring 59 is effective for returning the piston to the position shown in FIG. 10, closing flap valve 56, shown in dash lines in its open position.

The corresponding pressure relief valve 45, FIG. 11, includes a sleeve 95 at its inner end connected to the outer wall 47 of socket 31, and projects through an aperture 46 in prosthesis wall 21. The push button 54 is movably positioned within sleeve 95 and is biased outwardly to a normally closed position by coil spring 59 which bears against the stop or washer 97 and said button.

The inner end of rod 58 is connected to the valve 56 shown in dash lines in open position, and at its other end is connected to the push button 54. Limited inward movement of push button 54 will open the flap valve 56 sufficiently to permit escape of some pressurized air through the sleeve 95 and out the air outlet 48. On release of the button 54, spring 59 is effective for moving the button to the position shown closing the flap valve 56 due to the action of rod 58. Since foot 13 could be replaced with an arm assembly, as an equivalent construction, member 13 is sometimes referred to as an appendage.

Having described my invention, reference should now be had to the following claims:

I claim:

1. An insert unit for use with a prosthesis, said prosthesis having a hollow body of a predetermined cross sectional shape including stiff peripheral walls and a cup shaped concave partition defining with said walls an elongated first socket for receipt of said insert unit, said insert unit comprising:

a first member shaped substantially complimentarily to said socket having a concave bottom portion and continuous peripheral side walls, said bottom portion being supportably mounted upon said partition and said side walls frictionally engaging the peripheral walls of said socket;

a second member spaced inwardly of said first member having a base and continuous upstanding walls, said upstanding walls of said second member and said side walls of said first member being hermetically sealed to define a first continuous chamber between said first and second members, said first chamber containing air; and a third member spaced inwardly of said second member forming an elongated second socket for receipt of a human stump, said second socket having a continuous wall and base, said wall being hermetically sealed, adjacent the open end of said second socket, to said upstanding wall of said second member defining a sealed second continuous chamber therebetween, said second chamber containing liquid.

2. The insert unit of claim 1, further including a manually operated air pump mounted upon said first member having an air inlet communicating with said air chamber, said air pump adapted to apply air pressure to said air chamber.

3. The insert unit of claim 2, further including a manually operated pressure relief valve mounted upon said first member having a one way air outlet communicating with said air chamber for selectively exhausting air therefrom.

4. The insert unit of claim 3, wherein said pump and said relief valve project outwardly from said second member and protrude through the peripheral wall of said prosthesis.

5. The insert unit of claim 1, further including a manually operated air pump and a manually operated relief valve mounted upon said first member and located upon the medial side thereof.

* * * * *

UNITED STATES PATENT AND TRADEMARK OFFICE
CERTIFICATE OF CORRECTION

PATENT NO. : 4,655,779

DATED : April 7, 1987

INVENTOR(S) : Christopher S. Janowiak

It is certified that error appears in the above-identified patent and that said Letters Patent is hereby corrected as shown below:

Claim 4 line 2 "second" should read —first—

Signed and Sealed this

Fifteenth Day of September, 1987

*Attest:*

DONALD J. QUIGG

*Attesting Officer*   *Commissioner of Patents and Trademarks*